United States Patent [19]

Clarey

[11] 4,157,713
[45] Jun. 12, 1979

[54] AIR-PRESSURE SPLINT

[76] Inventor: Michael T. Clarey, 2825 Point Tremble Rd., Algonac, Mich. 48001

[21] Appl. No.: 795,960

[22] Filed: May 11, 1977

[51] Int. Cl.² .................................................. A61F 5/04
[52] U.S. Cl. ............................ 128/87 R; 128/DIG. 20
[58] Field of Search .......... 128/87 R, 84 R, DIG. 20, 128/93, 89 R

[56] References Cited

U.S. PATENT DOCUMENTS

| | | | |
|---|---|---|---|
| 2,387,192 | 10/1945 | Straits | 128/84 R |
| 2,531,074 | 11/1950 | Miller | 128/DIG. 20 |
| 2,694,395 | 11/1954 | Brown | 128/DIG. 20 |
| 3,074,398 | 1/1963 | Guiney | 128/DIG. 20 |
| 3,164,152 | 1/1965 | Nicoll | 128/DIG. 20 |
| 3,496,934 | 2/1970 | Anderson | 128/93 X |

*Primary Examiner*—John D. Yasko
*Attorney, Agent, or Firm*—Basile and Weintraub

[57] ABSTRACT

An air-pressure splint sized to fully encase an injured human leg. The splint comprises inner and outer flexible wall members which are joined to each other by seaming about the perimeter to define an air-tight sealed relationship between the walls forming a double-walled, sealed, inflatable envelope. The envelope has separable air-tight margins adapted to be releasably connected to each other by a zipper-type fastener to hold the pressure splint in a surrounding position around the human leg. The upper end of the envelope has an uneven peripheral contour such that a portion of the envelope end extends upward above the leg for restraining the splint against rotation about the injured leg when the splint is in an inflated mode.

2 Claims, 3 Drawing Figures

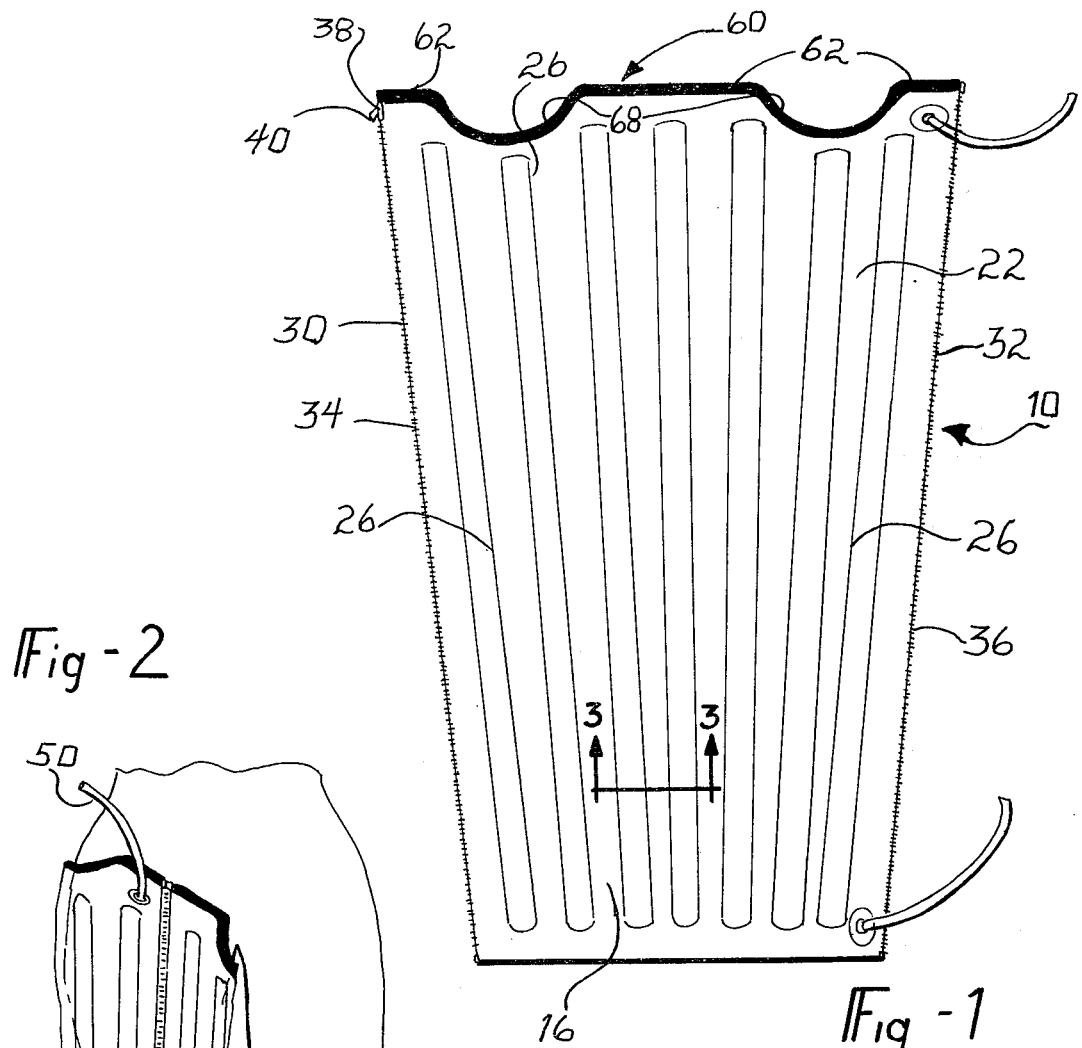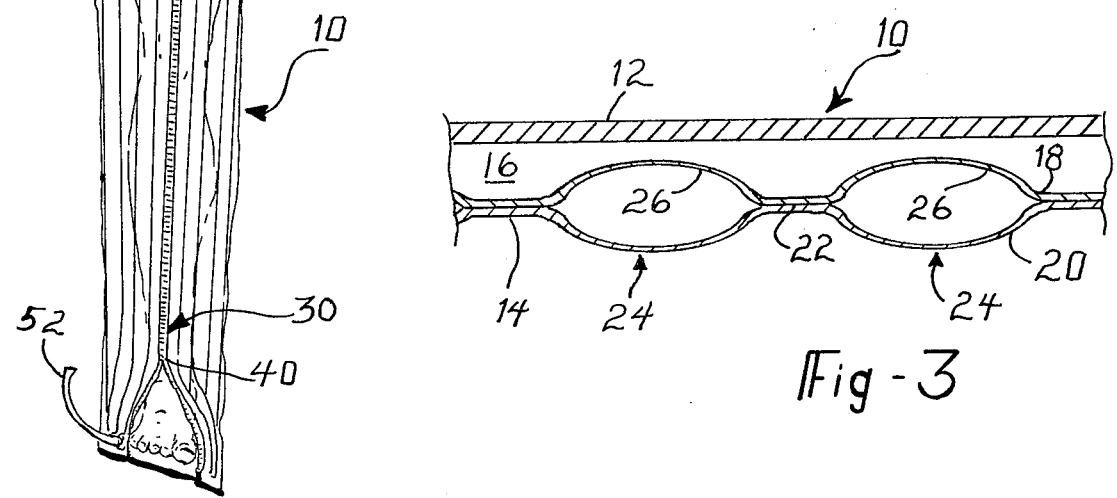

AIR-PRESSURE SPLINT

BACKGROUND OF THE INVENTION

I. Field of the Invention

The present invention relates to inflated splints for supporting injured human legs and, in particular, to an improved, pneumatically inflatable pressure bandage splint structure used in the emergency immobilizing of a leg fracture.

II. Description of the Prior Art

Many injuries and fractures to legs occur in locations that are distant from immediate, competent medical attention, and transportation of the injured person may be hazardous and painful resulting in further injury to the fractured leg. There is, therefore, a great need for a small, compact leg splint to meet emergencies of this type. Such a splint should meet several requirements as to size, ease of application and protection of the injured limb. As to size, the splint should be such as to be capable of being folded into a compact small size that can fit into a first-aid kit to be easily carried in an ambulance or the like. Secondly, the splint should be capable of being properly applied by a person other than a medical doctor and without further injury or damage to the broken leg. Thirdly, the splint should properly support the injured leg to render the fractured portion immobile and should be comfortable on the leg. Preferably, in this connection, it is desirable that the clothing of the injured party remain on the person to protect the person against weather and avoid possible further injury to the person by the removal of the clothing. Several attempts have been made to meet these basic requirements, and examples of such attempts are disclosed in U.S. Pat. Nos. 2,651,302; 3,164,152; 3,351,055; and 3,605,737. Each of these patents is relevant to applicant's invention in that they deal with apparatuses for immobilizing a limb fracture. However, in the opinion of applicant, they are not capable of being utilized for immobilizing an injured knee joint or maintaining traction on an injured femur with the ease and speed that is necessary to ensure the proper application of the splint to the injured person and without appreciable movement to the injured leg.

PRIOR ART STATEMENT

In the opinion of applicant, the above-mentioned patents represent the closest prior art of which applicant is aware.

SUMMARY OF THE INVENTION

The present invention, which will be described subsequently in greater detail, comprises an air-pressure splint for fully encasing an injured human leg wherein the air splint is of a double-walled envelope construction having sealed ends and containing air under pressure. Provisions are made to equip corresponding margins of the envelope with slide fastener means enabling the splint to be applied to an injured limb in an opened condition along such margins without significantly moving the limb and then closed about the limb by manipulation of the zipper fastening means prior to inflation of the air splint. The upper ends of the envelope have an uneven peripheral contour such that a portion of the envelope extends upwardly above the leg and, upon inflation of the envelope, functions to retain the splint from rotating about the leg.

It is therefore a primary object of the present invention to provide an air-pressure splint for surrounding an injured leg and which is provided with means for preventing the splint from rotating with respect to the leg once the splint has been inflated.

It is a further object of the present invention to provide an air-pressure splint capable of maintaining traction on the injured leg, as an emergency treatment of a fractured femur.

It is a further object of this invention to provide an air-pressure splint that may be folded away into a small, light compact package and which can be easily and properly applied to support an injured leg by a person having minimal medical training.

It is a further object of the present invention to provide an air-pressure splint which is of a one-piece construction and of a design which is simple and inexpensive to manufacture.

It is a further object of this invention to provide an air-pressure splint which can be quickly applied to an injured leg and is of such a construction that it minimizes loss of blood due to the circumventional pressure around the limb and, because of its size, may function as a knee splint which may be retained on the patient while at the hospital and may be retained on the patient during the use of X-ray inspection of the leg.

Other objects, advantages and applications of the present invention will become apparent to those skilled in the art of air-pressure splints when the accompanying description of one example of the best mode contemplated for practicing the invention is read in conjunction with the accompanying drawing.

BRIEF DESCRIPTION OF THE DRAWING

The description herein makes reference to the accompanying drawing wherein like reference numerals refer to like parts throughout the several views, and wherein:

FIG. 1 is a plan view of the outer face of an air-pressure splint constructed in accordance with the principles of the present invention and laid flat as it might appear when not in use;

FIG. 2 is a front plan view illustrating the manner in which the air-pressure splint illustrated in FIG. 1 of the drawing is wrapped about the leg of a person; and FIG. 3 is an enlarged, fragmentary cross-sectional view of the air-pressure splint taken along Line 3—3 of FIG. 1.

DESCRIPTION OF THE PREFERRED EMBODIMENT

Referring now to the drawing and, in particular, to FIGS. 1 and 3 wherein there is illustrated one example of the present invention in the form of an air-pressure splint 10. The improved air-pressure splint 10 comprises an outer wall 12 and an inner wall 14. The walls 12 and 14 are preferably fabricated from a fully transparent material, such as a plastic material. The walls 12 and 14 are readily flexible and retain air pressure in the air chamber 16 defined between the walls 12 and 14. The two sheets must be adequately flexible, but sufficiently rigid, so as not to deform under the pressures involved in their use as an air-pressure splint 10. The inner wall 14, however, must be of sufficient flexibility and pliable to conform readily to the shape of the limb on which the air-pressure splint 10 is inflated. To this end, the inner wall 14 actually comprises two sheets 18 and 20 which are intermittently secured by an adhesive or the like, as at 22, such that the unsecured portions 24 define an inflatable rib section 26 that extends substantially the full length of the wall 14 (FIG. 1). The rib sections 26 are intermittently and symmetrically arranged between the marginal side areas 30 and 32 of the air splint 10 and preferably in uniformly spaced relationship to each other and to the series of uninflated strips 22. The parallel, inflatable spaces or cells 26 add to the flexibility of the inner surface 20 such that it readily conforms to the shape of the limb while providing support and protection for the fractured limb.

As can best been seen in FIGS. 1 and 2, the air-pressure splint 10 is completed by slide fastener members 34 and 36 which are fixedly applied to portions of the longitudinal envelope margins. It will be observed in FIG. 2 that the slide fastener elements 34 and 36 are orientated in the longitudinal sense relative to the envelope margins reversely of the usual fashion; that is, it is intended that the splint 10 may be closed by the slide fastener generally designated 38 by manipulating its movable tongue piece 40 from the top of the fastener 38 which is fully opened before application of the splint 10 to the bottom. Thus, the lower portion of the splint 10 may be brought snugly around the upper portion of the injured person's foot regardless of the particular size of the foot or the length of the injured person's leg. The slide fastener 38 is of the usual, conventional self-locking type, enabling the air-pressure splint 10 to remain snug on the limb when inflated for the desired splinting effect. "Velcro" type fasteners may be used.

The air-pressure splint 10 is provided with a pair of valved inflating tube members 50 and 52 applied to the outer wall 12 of the splint 10. The splint is inflated orally at one or both of the members 50 and 52. The use of two valve members permits the two parties' applying the splint to both simultaneously pressurize the air-pressure splint 10. It should be noted that both of the air valves 50 and 52 are provided with lengthy air tubes. This permits the same air-pressure splint 10 to be applied to either leg of a person, providing easy accessibility to the valves 50 and 52 by the users. Suitable plugs may be applied to the ends of the tubes to seal them once the air-pressure splint 10 has been fully inflated.

As can best be seen in FIGS. 1 and 2, the upper peripheral edge 60 of the splint 10 is provided with an uneven contour having raised sections 62 adjacent the slide fastener's longitudinal edges and a mid-section which is similarly raised. The sections 62 are separated by circular recessed areas 68. This uneven contour 60 permits the adaptability of the air-pressure splint 10 to either leg of a human person with the recessed portions 68 being adapted to be received in the crotch portion of an individual, while the sections 62 will generally be disposed in the front and rear of the individual substantially above the crotch portion, as shown in FIG. 2. When the air-pressure splint 10 is inflated, these sections 62 are similarly inflated and provide a substantial means for restraining the splint 10 from rotating about the injured person's leg, all of which functions to prevent further injury and discomfort to the injured person.

In use, while traction is being applied to the limb at the ankle, the air-pressure splint 10 is placed on the leg from high in the crotch area, as illustrated in FIG. 2, extending to a point past the bottom of the foot, as shown. The oversized slide fastener 38 is zipped from the crotch area along the top of the splint 10 to the instep of the foot. With the splint enclosing the whole of the leg, the splint 10 is pulled snugly into the crotch and held in place while the splint 10 is inflated by means of the inflation valves 50 and 52. The splint 10 is inflated to a pressure sufficient to maintain the traction. Obviously, the traction must be held in place manually until the air-pressure splint has been fully inflated.

It can be seen that applicant's splint 10 provides numerous advantages over the prior art and that it can be made of relatively inexpensive materials. Because of its unique shape and construction, it may be speedily, simply and easily applied to the injured leg. Because of its construction, it may be rolled up and stored in approximately a six-inch squared area.

The air-pressure splint provides padding over the entire wound, thus aiding in the traction of the leg, as well as providing additional comfort to the injured person. Because the pressure is applied in a uniform manner over the entire leg, the air-pressure splint 10 keeps blood loss to a minimum and, thus, prevents or at least minimizes traumatic shock.

Because the transparent material is utilized, X-ray treatment may be carried out without the necessity of removing the splint.

It should be understood by those skilled in the art of air-pressure splints that other forms of applicant's invention may be had, all coming within the spirit of the invention and scope of the appended claims.

What is claimed is as follows:

1. An air-pressure splint for fully encasing an injured human leg, said air-pressure splint comprising:

an outer flexible and relatively non-stretchable wall;
an inner flexible wall connected by seaming about its perimeter in air-tight, sealed relationship to said outer wall to coact with the latter and defining a double-walled and sealed, inflatable envelope, said envelope including an air chamber portion in position to surround the entire leg,
an inner flexible wall disposed between said inner wall, said outer wall intermittently connected to the outer wall by air-tight margins forming a plurality of longitudinally disposed laterally spaced air chambers, said air chambers releasably engaging said inner wall to hold said chamber portion in said surrounding position;
releasable, self-locking, slide fastener connecting means longitudinally disposed on said respective separate margins extending from the upper adjacent corresponding ends of the latter to the opposite lower margin ends at the foot portion of said air splint for releasably connecting the margins together with the chamber portion of the splint surrounding the injured leg, said slide fastener closing as the slide is moved toward the foot portion, the splint having a length to extend beyond the foot a distance, said slide adapted to come to rest against the upper portion of the foot and adapted to exert a slight force on the top of the foot and preventing rotation of said splint and longitudinal traction of the leg;
the upper ends of said envelope having uneven peripheral contours such that a portion of said envelope end extends upwardly above said leg for restraining said splint from rotating about said leg and exerting an upward pressure on the crotch when said envelope is inflated.

2. The air-pressure splint defined in claim 1 wherein said inner flexible wall is comprised of a plurality of longitudinally disposed and laterally spaced air chambers.

* * * * *